United States Patent
Fatho et al.

(10) Patent No.: US 8,349,558 B2
(45) Date of Patent: Jan. 8, 2013

(54) DETECTION OF INDIVIDUAL T-CELL REACTION PATTERNS AGAINST TUMOR-ASSOCIATED ANTIGENS (TAA) IN TUMOR PATIENTS AS A BASIS FOR THE INDIVIDUAL THERAPEUTIC VACCINATION OF PATIENTS

(75) Inventors: Martina Fatho, Wörrstadt (DE); Emmanuelle Wesarg, Darmstadt (DE); Volker Lennerz, Ober-Olm (DE); Pierre Van Der Bruggen, Brussels (BE); Thomas Wölfel, Mainz (DE); Serena Debo, Mainz (DE)

(73) Assignee: Johannes Gutenberg-Universitat Mainz, Mainz (DE)

( * ) Notice: Subject to any disclaimer, the term of this patent is extended or adjusted under 35 U.S.C. 154(b) by 594 days.

(21) Appl. No.: 12/519,315

(22) PCT Filed: Nov. 28, 2007

(86) PCT No.: PCT/EP2007/010329
§ 371 (c)(1),
(2), (4) Date: Oct. 28, 2009

(87) PCT Pub. No.: WO2008/080468
PCT Pub. Date: Jul. 10, 2008

(65) Prior Publication Data
US 2010/0035267 A1 Feb. 11, 2010

(30) Foreign Application Priority Data
Dec. 21, 2006 (DE) .......................... 10 2006 060 824

(51) Int. Cl.
*C12N 33/48* (2006.01)
*C12N 5/02* (2006.01)
*G01N 33/48* (2006.01)
*C12N 5/10* (2006.01)

(52) U.S. Cl. ........... 435/6.1; 435/7.24; 435/374; 436/63

(58) Field of Classification Search .................. None
See application file for complete search history.

(56) References Cited

FOREIGN PATENT DOCUMENTS

| DE | 10 2005 041616 |   | 3/2007 |
|----|----------------|---|--------|
| WO | WO94/02156     | * | 2/1994 |
| WO | WO 2005/028505 |   | 3/2005 |
| WO | WO 2007/025760 |   | 3/2007 |

OTHER PUBLICATIONS

Heiser et al (Journal of Immunology, 2001, vol. 166, pp. 2953-2960).*
Britten et al (Journal of Immunological Methods, 2004, vol. 287, pp. 125-136).*
Scanlan et al (Immunological Reviews, 2002, vol. 188, pp. 22-32).*
Urban and Schreiber (Ann Rev Immunol, 1992, vol. 10, pp. 617-644).*
Van Baren et al (Journal of Clinical Oncology, 2005, vol. 23, pp. 9008-9021).*
Javorovic et al., "RNA transfer by electroporation into mature dendritic cells leading to reactivation of effector-memory cytotoxic T lymphocytes: a quantitative analysis", *Molecular Therapy*, Oct. 2005, vol. 12, No. 4, pp. 734-743.
Lennerz et al., "The response of autologous T cells to a human melanoma is dominated by mutated neoantigens", *Proceedings of the National Academy of Sciences of USA*, Nov. 2005, vol. 102, No. 44, pp. 16013-16018.
Liao et al., "Transfection of RNA encoding tumor antigens following maturation of dendritic cells leads to prolonged presentation of antigen and the generation of high-affinity tumor-reactive cytotoxic T lymphocytes", *Molecular Therapy*, May 2004, vol. 9, No. 5, pp. 757-764.
Nair et al., "Induction of tumor-specific cytotoxic T lymphocytes in cancer patients by autologous tumor RNA-transfected dendritic cells", *Annals of Surgery*, Apr. 2002, vol. 235, No. 4, pp. 540-549.

* cited by examiner

*Primary Examiner* — Karen Canella
(74) *Attorney, Agent, or Firm* — Saliwanchik, Lloyd & Eisenschenk

(57) ABSTRACT

The present invention relates to a method for identifying the preferential target antigens of antitumoural T-cells of a tumour patient, comprising: a) providing T-cells from the blood of at least one tumour patient, b) providing dendritic cell (DCs) and/or B-lymphocytes (BLCs) that are autologous for said tumour patient, wherein said DCs and BLCs were transfected beforehand with a selection of mRNAs encoding for T-cell-immunogenic tumour-associated antigens (TAA), and express these, c) contacting said T-cells with the DCs and/or BLCs, d) identifying of those T-cells that recognize antigens of the DCs and/or BLCs, and e) identifying of the preferential target antigens of antitumoural T-cells of the at least one tumour patient on the basis of the T-cells that recognize antigens of the DCs and/or BLCs. The method can furthermore comprise the expansion of the T-cells that recognize the antigens of the DCs and/or BLCs. The present invention furthermore relates to a method for producing an individualized tumour vaccine or individualized tumour therapeutic, as well as corresponding methods for treating a tumourous disease using the individualised tumour vaccine or individualised tumour therapeutic.

13 Claims, 5 Drawing Sheets

Figure 1:
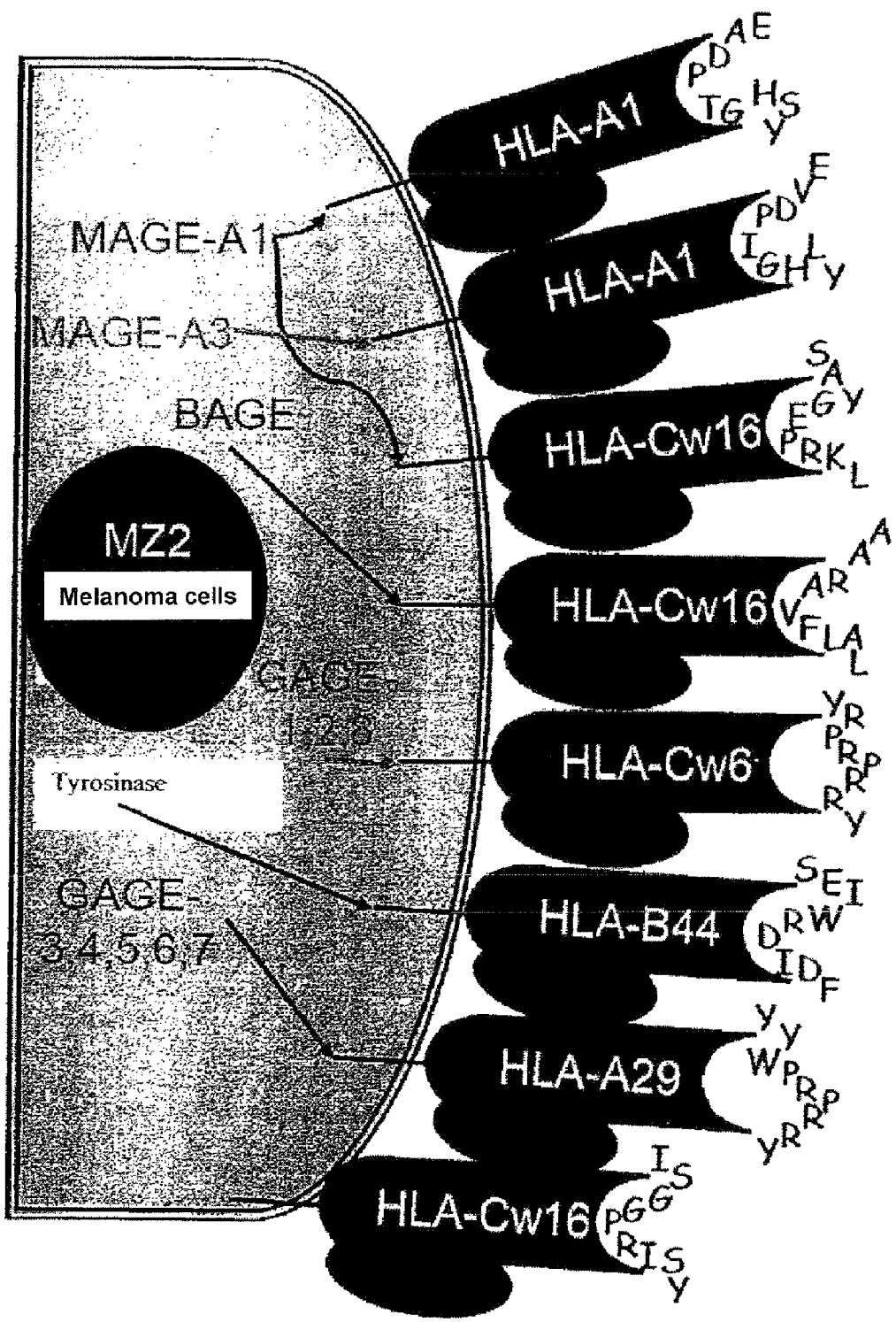

DETECTION OF INDIVIDUAL T-CELL REACTION PATTERNS AGAINST TUMOR-ASSOCIATED ANTIGENS (TAA) IN TUMOR PATIENTS AS A BASIS FOR THE INDIVIDUAL THERAPEUTIC VACCINATION OF PATIENTS

CROSS-REFERENCE TO A RELATED APPLICATION

This application is a National Stage Application of International Application Number PCT/EP2007/010329, filed Nov. 28, 2007; which claims priority to Germany Patent Application No. 10 2006 060 824.0, filed Dec. 21, 2006; all of which are incorporated herein by reference in their entirety.

The present invention relates to a method for identifying the preferential target antigens of antitumoural T-cells of a tumour patient, comprising: a) providing T-cells that are not stimulated by a contact with a tumour cell line in vitro from the blood of at least one tumour patient, b) providing dendritic cells (DCs) and/or B-lymphocytes (BLCs) that are autologous for said tumour patient, wherein said DCs and BLCs are transfected beforehand with a selection of mRNAs encoding for T-cell-immunogenic tumour-associated antigens (TAA) and express these, c) contacting said T-cells with said DCs and/or BLCs, and d) identifying TAAs that are recognized by T-cells on transfected DCs and/or BLCs. The method can further comprise the expansion of T-cells that recognize the antigens of the DCs and/or BLCs. The present invention furthermore relates to a method for producing an individualized tumour vaccine or individualized tumour therapeutic, as well as corresponding methods for treating a tumourous disease using the individualised tumour vaccine or individualised tumour therapeutic. Cancer cells express a multitude of tumour associated antigens (TAAs). It was shown in human in vitro-models that the recognition of oligopeptides from TAAs by tumour reactive cytotoxic T-lymphocytes (CTL) leads to the destruction of the tumour cells. CTLs recognize oligopeptides that stem from cytoplasmatically degraded proteins and are presented by molecules of the major histocompatibility complexes (HLA-classes I and II) on the cellular surface.

One particular approach is represented by the specific active immunotherapy, which sensitizes the immune system of the patient against TAAs on the tumour cells and which shall induce a long term immunity. Thus, in the context of the immunotherapy, vaccines are applied to the patient that contain the respective TAAs. So far, approaches of cancer immunotherapy were limited to the use of a few TAAs from the categories of differentiation and cancer/germ line-antigens (C/G-antigens) that are commonly expressed in tumour tissues, and from which peptides are presented by those HLA-alleles that are occurring most frequently in the population. Thereby, it was not analyzed whether the patients of the study were generally able to generate an immune response against the vaccination antigens (Rosenberg et al., Nat. Med. 10: 909, 2004). It was attempted by Japanese research groups to individualize the vaccination with peptides from TAA in lung carcinoma patients and patients with gastrointestinal tumours by an advance testing of the peripheral blood lymphocytes for a reactivity against candidate peptides from TAA. Only peptides against which a reactivity could be shown were used for a vaccination (Mine et al., Cancer Sci. 94: 548, 2003; Sato et al., Cancer Sci. 94: 802, 2003). The selection of the candidate peptides from the TAAs was limited to HLA-A2- and HLA-A24-binding peptides. Indeed, these are the most commonly occurring HLA-alleles in the Asian population groups, but therefore the method is only available for HLA-A2- and -A24-positive patients. T-cell responses against peptides from the identical TAAs that are presented by other HLA-alleles can not be encompassed by the method. Furthermore, the method was based on the stimulation of peripheral T-cells of the patients with the candidate peptides. In the meantime, several studies have shown that those methods admittedly lead to the expansion of peptide specific T-cells, but that the T-cells often do not recognize the tumour cells. This is either based on the fact that the tumour cells do not process and present the peptide from the TAA, or that the T-cells react only to the high peptide concentrations that are used for the stimulations, but not to the markedly lower concentrations of the peptides that are displayed naturally on the tumour cells.

Other groups compared normal kidney tissue with tumour tissue with respect to differences in the global expression of genes and differences in the presentation of MHC class I-peptides in renal carcinoma patients after nephrectomy. The "gene profiling"-analyses led to the identification of tumour specifically expressed or over-expressed genes. The mass spectrometry analyses of the biochemically purified HLA-peptides isolated the natural HLA-ligands of the tumour-specific or over-expressed proteins (Weinschenk et al., Cancer Res. 62: 5818, 2002). Large amounts of both tissues are needed for the comparative "gene profiling", and the comparative analysis of the natural HLA-peptide ligands of tumour and normal tissue. Therefore, this method is only suitable for a few types of tumours and only in progressed tumourous disease. The authors of the above-cited work, in an actual review article, estimate that the sensitivity of their method allows them to identify at most 4% of the natural HLA-ligands from a tissue sample (Rammensee, Immunology and Cell Biology 84: 290, 2006). In addition, only very few of the peptides as identified by this way indeed have a tumour specificity that appears to be sufficient, and it is not clear whether these peptides can trigger T-cell responses. A further possibility of the individual specific cancer immunotherapy is the vaccination of the patients with their own tumour cells or products of the tumour cells such as, for example, heat shock proteins/peptide complexes (Srivastava, Curr. Opin Immunol. 18: 201, 2006). Tumour cells can be injected alone or admixed with dendritic cells (O'Rourke et al., Cancer Immunol. Immunother. 52: 387, 2003). Furthermore, the possibility exists to render the tumour cells more immunogenic before the application by gene therapy methods. The immunisation with tumour cells alone or in admixture, or fused with dendritic cells or tumour-heat shock proteins, respectively, to which the TAA-peptides are bound, requires larger amounts of tumour material for the preparation of the vaccine. This, in the clinical routine, not uncommonly is a limiting factor for such a strategy. It was shown for many types of cancers that they express several TAAs at once. For example, in 40% of breast tumours, 65% of malign melanomas, and 37-57% of lung tumours, the simultaneous expression of several C/G antigens can be found (Simpson et al., Nat. Rev. Cancer 5: 615, 2005). In case of the malign melanoma, more than 90% of the tumours additionally express differentiation antigens (Boon et al., Ann. Rev. Immunol. 24: 175, 2006). In general, therefore only a few of the vaccination studies take into consideration the individual character of the tumour-host-interactions in cancer patients.

DE 10 2005 041 616 describes certain melanoma-associated oligopeptides that are recognized as peptide antigen by CD8-positive cytotoxic T-lymphocytes (CTLs) and lead to a CTL-induced lysis and/or apoptosis of tumour cells. Furthermore, the present invention relates to the use of these melanoma-associated oligopeptides in cancer therapy.

DE 10 2005 013 846 describes a strategy for an identification and provision of tumour-associated expressed antigens and nucleic acids encoding these. This strategy is based on the analysis of human protein and nucleic acid data bases with a view on potential cancer specific antigens that are accessible on the cellular surface. By data-mining, first a list of all known genes is generated that is as complete as possible, which, following the basic principle of gene to mRNA to protein, is examined for the presence of one or more transmembrane domains. Following this are a homology search, a grouping of the hits into tissue specific groups (amongst others, tumour tissue), and a check for the real existence of the mRNA. Finally, the proteins so identified are evaluated, e.g. by expression analyses and protein-chemical methods, for their aberrant activation in tumours.

The knowledge about the preferential target antigens of the immune system of a patient could lead to the production of a TAA-vaccine that is tailor-made for the patient that could be used for an effective therapeutic vaccination. It is therefore an object of the invention, to provide a method for the identification of tumour-specific T-cell responses from the peripheral blood of individual patients, and their target antigens. On the basis of this method, also further advantageous embodiments of the invention shall be provided.

In a first aspect of the present invention, this object is solved by a method for identifying of those TAAs of a tumour patient that are T-cell-immunogenic, wherein said method comprises a) providing of T-cells from the blood of a least one tumour patient, b) providing of dendritic cells (DCs) and/or B-lymphocytes (BLCs) autologous for the tumour patient, wherein the DCs and BLCs have been transfected beforehand with a selection of mRNAs encoding for T-cell-immunogenic tumour-associated antigens (TAA), and expressing these, c) contacting of the T-cells with the DCs and/or BLCs, d) identifying those T-cells that recognize antigens of the DCs and/or BLCs, and e) identifying of the antigen-expression pattern of the at least one tumour patient, based on those T-cells that recognize antigens of the DCs and/or BLCs.

Mitchell and Nair (Mitchell and Nair, RNA-transfected dendritic cells in cancer immunotherapy. J Clin Invest. 2000 November;106(9):1065-9) and Nair et al. (Induction of tumour-specific cytotoxic T lymphocytes in cancer patients by autologous tumour RNA-transfected dendritic cells. Ann Surg. 2002 April;235(4):540-9.) relate to the possibility, to use dendritic cells (DCs) transfected with tumour(-whole)-mRNA ("mRNA encoding the antigenic content of the tumour cell") as a tumour cell surrogate. These tumour cell-equivalents shall be used for vaccinations, the monitoring of T-cell responses as generated, and for the identification of new TAAs. Except for the fact that with the RNA-transfected DCs the identical antigen-presenting cells (APC) are used in order to stimulate T-cells of a tumour patient ex vivo, the present invention has nothing in common with this method as published. It is known from a series of patient models that patients with metastasising malignomas show antitumoural T-cell responses in the blood. These T-cells mostly recognize only a very limited subset of the TAAs as expressed by the tumour, and in view of the actual peptide epitopes and the HLA-alleles recognizing these peptides, the recognition is highly individual-specific.

Many methods of the state of the art (including the one as described in Mitchell and Nair, above) relate to the identification of genes that are specifically expressed in the tumour, which then shall serve as potential targets for cancer immunotherapy. Nevertheless, the expression of a tumour antigen does not mean that it is also immunogenic. In addition to the expression, its immunogenicity decisively depends from the fact whether peptides are processed out of said TAA-protein and can be bound to the individual HLA-molecules of the respective patient, and whether the T-cell repertoire of the patient can recognize the HLA-peptide complexes. From this, it follows that from at least several dozens (as known today) of potentially immunogenic TAAs only very few peptides from individual TAAs actually provoke a T-cell response in the individual patient, which, nevertheless, can only be predicted insufficiently. For a solution of this problem, the present invention provides the stimulation and testing assay according to the invention. It shall identify those T-cell responses that have been generated in patients through an interaction with the tumour cells, and that can be activated. The reactivity is confirmed in the subsequent ELISPOT assay by the cytokine release upon antigen-contact. Then, detectable T-cell responses can subsequently be specifically amplified by a vaccination.

This represents the essential difference compared with all vaccination studies that have been performed so far. These were targeted at the amplification and generation, respectively, of responses against "desired antigens" for which the expression in the respective tumour was indeed given, but for which there was no evidence whether they would be at all immunogenic in the vaccinated patient. In contrast to the methods as above, the present method according to the invention is truly independent from the generation of tumour cells from the patient.

Preferred is a method according to the present invention which furthermore comprises the expansion of the T-cells that recognize antigens of the DCs and/or BLCs. Further preferred is a method according to the present invention which furthermore comprises a control assay for the reactivity of the T-cells against the TAAs. Respective methods are known to the person of skill, and are exemplarily described in the examples below (e.g. IFN-g-ELISPOT-assay). An even further preferred method according to the present invention further comprises the detection of the restringing HLA alleles that present the TAAs as recognized. Preferred HLA-alleles are selected from Cw16; Cw6; Cw7; Cw2; Cw3; DP4; DR1; DR2; DR3; DR4; DR7; DR11; DR12; DR13; DR15; DR8; DR52; A1; A2; A3; A29; A24; A31; A34; B7; B13; B15; B35; B37; B51; B53; B57; B337; B18; B40; B44; B52; DQ6; DP4; DP1; DP10; and A68. Respective methods are known to the person of skill, and are exemplarily described in the examples below. The method according to the present invention has several advantages: In contrast to earlier methods, the method is independent from the generation of a stable tumour cell line, which was required earlier for the expansion of tumour-specific T-cells. Instead, T-cells from the peripheral blood of tumour patients are stimulated with—preferably autologous—dendritic cells (DCs) or B-lymphocytes (BLCs) that were transfected beforehand with a selection ("panel") of mRNAs encoding for T-cell-immunogenic tumour-associated antigens (TAAs). The panel comprises antigens of several categories, in particular antigens of the differentiation and cancer/germ line-type. In the context of the present invention, in a short-term stimulation protocol, T-cells from the peripheral blood of tumour patients were expanded in individual settings with up to 35 immunogenic TAAs. Dendritic cells or B-cells of the respective patient were used as antigen-presenting cells that were provided with antigen-encoding mRNA. The responder-lymphocytes of these stimulation reactions were tested for the recognition of these TAAs, and their HLA-restriction elements were determined.

The stimulation and reactivity assay allows for the identification of an individual spectrum of the target antigens of anti-tumoural T-cells, independently from the availability of autologous tumour cells. So far, these examinations were only possible in those few patient models, where a stably growing cell line could be established from the respective tumours which then was employed for the stimulation and expansion of tumour-reactive T-cells. T-cells that recognize respective antigens from this panel are preferably expanded and could, for example, be used for the additional methods according to the invention and/or in pharmaceutics. The recognition pattern of the T-cells, as expected, is largely specific for the individual patient; the individual reaction pattern is dictated by the antigen-expression pattern of the individual tumour, the individual HLA-phenotype, and the capacity of the individual T-cell repertoire to generate an antigen-specific response against the respective HLA-peptide complexes. In a subsequent reaction assay as described herein, the reactivity of the T-cells against the stimulation antigen can be confirmed, and the restringing HLA-alleles could be detected that present the TAA-peptides as recognized.

In a further aspect of the method according to the invention, the T-cells are isolated from the peripheral blood of the tumour patient. Nevertheless, also other common sources of T-cells can be used.

Preferred is a method according to the present invention, wherein the mRNAs as transfected into the DCs or BLCs are selected from antigens of several categories, namely differentiation antigens, C/G-antigens, mutated antigens, and over-expressed antigens. The inventors chose the messenger-RNA (mRNA) as antigen format. mRNA is suitable for the transient transfection of a multitude of kinds of cells, encodes for the antigens in full length, and thus includes the entirety of possible epitopes. In some earlier studies, the suitability of mRNA-transfected DCs for the detection of T-cell responses was analyzed (Britten et al., J Immunol Methods 287:125, 2004; Britten et al., J Immunol Methods 299:165, 2005). For the test as planned, in vitro transcribed (IVT) TAA-encoding mRNAs are transfected into mDCs from the peripheral blood of the respective patients. RNA-transfected DCs will then serve as stimulator cells for the expansion of the TAA-reactive T-cells.

Based on their expression patterns, tumour associated antigens (TAA) can be divided into several categories:
a) Differentiation antigens are only expressed in tumours and cells of the type of tissue, from which they are generated. For example, differentiation antigens of the malign melanoma (MM) are melanocyte-specific proteins, such as tyrosinase, tyrosinase-related protein-2 (TRP-2), gp100, and melan-A/MART-1.
b) Apart from gametes and trophoblast cells, "cancer/germ line"-antigens (C/G-antigens, "shared tumour-specific") are not expressed in any other differentiated tissue. Epigenetic changes due to the malign transformation lead to the aberrant expression of C/G-antigens in cancer cells. Most tumour cells simultaneously express several C/G-antigens, and their expression is maintained during the course of the tumour progression. In addition, C/G-antigens are expressed in a large number of tumours of several histologies.
c) Antigens that carry "missense"-point mutations, and fusion proteins that are generated through tumour specific translocations of gene segments, are grouped into the category of mutated antigens. Apart from very few exceptions, the point-mutated antigens that are known so far are specific for the individual tumour, in which they were discovered. In contrast, malignoma-specific fusion proteins, such as, for example, BCR/ABL (in chronic myelotic leukaemia) are commonly found in haematologic cancerous diseases.
d) As the fourth category of TAAs, over-expressed antigens can be found in tumours. These include proteins that are expressed strictly regulated in cells of differentiated normal tissue, since many of these themselves regulate functions such as growth, cell cycle, apoptosis and the like.

Preferred is a method according to the invention, wherein the differentiation antigens are selected from melanocyte-specific proteins, such as tyrosinase, tyrosinase-related protein-2 (TRP-2), gp100, and melan-A/MART-1, or C/G-antigens, such as MAGE, GAGE, BAGE (regarding this, see also FIG. 1). Further preferred is method according to the invention, wherein the mutated antigen is selected from a fusion protein, e.g. from BCR/ABL and other known cancer-relevant fusions. In a further aspect of the method according to the invention, based on the above method an individualized TAA-recognition pattern by T-cells of a tumour patient is identified. According to the invention, this individual antigen-expression pattern serves as the essential basis for the generation of patient specific ("personalized") tumour vaccines. Such a vaccine can also be produced for an antigen-expression pattern that is identified according to the invention from a group of tumour patients that are suffering from a particular tumour. Thereby, particular types of tumours can be selectively treated in a patient group. Suitable groups would be, for example, tumours in kidney, breast, pancreatic, stomach, testicular, prostate, colon and/or skin cancer.

In a further aspect of the invention, the T-cell-stimulation assay as presented allows for the detection of structurally normal ("shared") antigens that can be recognized by autologous antitumoural T-cells in a large patient group. Thereby, tests are run against a broad spectrum of defined TAAs, taking into account the entirety of individual HLA-alleles. Only through this, the full potential of these antigens is made use of. The knowledge of the preferential target antigens of the immune system of a patient could lead to the production of a TAA-vaccine that is tailor-made which can be used for a therapeutic vaccination for a patient. Therefore, particularly preferred is a method according to the invention, wherein the antigen-expression pattern of a group of tumour patients is identified, whose tumours express structurally normal ("shared") TAAs.

These TAAs are grouped using the term "shared antigens", and the expression thereof was detected in different tumours of the same origin of tissue (e.g. "differentiation antigens" in melanomas) or in tumours of different histologies. "Overexpressed antigens" and so-called "cancer/germ line-antigens" (the latter are also designated as "shared tumour-specific") belong to TAAs that are expressed in very different tumours. As mentioned, the term "shared" only relates to the expression of the antigens, which is shared by different tumours, but not to their immunogenicity. It was detected in different melanoma patients that their tumours expressed multiple antigens of all four categories (cancer/germ line-, differentiation, over-expressed, and mutated antigens). But only a fraction of these and only very different TAAs were T-cell-immunogenic in the respective patient. In addition, the specificity of the T-cell responses (what peptide from the TAA was presented by what HLA-molecule and recognized) was largely specific for the respective patient. Thus, for the intended examinations, all "shared" antigens are of interest, since they are potentially immunogenic.

Particularly preferred "shared" antigens in the sense of the present invention are (positions in brackets) BAGE-1; GAGE-1,2,8; GAGE-3,4,5,6,7; GnTV (intron); HERV-K-MEL; KK-LC-1; KM-HN-1; LAGE-1; MAGE-A1; MAGE-A2; MAGE-A3; MAGE-A4; MAGE-A6; MAGE-A9;

MAGE-A10; MAGE-A12; MAGE-C2; mucin; NA-88; NY-ESO-1/LAGE-2; SAGE; Sp17; SSX-2, SSX-4; and TRP2-INT2 (intron 2).

In a further aspect of the invention, it relates to a method for identifying a tumour in a patient, first comprising a method as mentioned above, and identifying of the tumour, based on the antigen-expression pattern of the tumour patient as determined. In a further aspect of the invention, it relates to a method for producing an individualized tumour vaccine, comprising a method as mentioned above, and formulating of the identified TAA/TAAs into a tumour vaccine. In a still further aspect of the invention, it relates to a method for producing an individualized tumour therapeutic, comprising a method as mentioned above, and formulating of the expanded identified autologous DCs and/or BLCs into a tumour therapeutic. From a selection of, in principle, immunogenic tumour antigens, those are selectively filtered out that are immunogenic in the given patient. These antigens then preferably can be used in a multiepitope-vaccine for the therapeutic immunization of the respective patient. A therapeutic vaccination with these antigens promises markedly better clinical results than the vaccination with antigens, from which it is not clear, if, in the individual case, an immune response is even possible at all. Since the assay does not require tumour cells, it can be generally used for all patients, whose tumours express the panel antigens or a fraction thereof. The independence from tumour cells makes it possible to use the assay also in patients that are clinically free of tumours, but have a high risk for a relapse of the tumourous disease. Particularly these patients are regarded as ideal candidates for the therapeutic vaccination.

Thereby, the tumourous diseases to be treated comprise, e.g., kidney, breast, pancreatic, stomach, testicular and/or skin cancer. Thereby, the listing of the tumourous diseases is only exemplary and shall not limit the field of use. It is known in the state of the art that specially generated T-cells that were specific for certain peptides could effectively and selectively kill tumour cells. In general, several application forms are possible for the use of tumour-associated antigens in a tumour vaccine. Thus, Tighe et al (Gene vaccination: plasmid DNA is more than just a blueprint, Immunol. Today 19(2):89-97, 1998) described that the antigen can be administered either as recombinant protein together with suitable adjuvants or carrier systems, respectively, or as the cDNA encoding for the antigen in plasmid vectors. In these cases, the antigen must be processed by antigen-presenting cells (APC) in the body of the patient, and be presented in order to thereby trigger an immune response. Melief et al. (Peptide-based cancer vaccines, Curr. Opin. Immunol. 8:651-657, 1996) showed a further possibility, namely the use of synthetic peptides as vaccines. In addition, also the administration of the TAA-RNA(s) that are recognized by T-cells as (multiepitope-)vaccine is possible. RNA can be used directly or in the form of transfected DCs.

Thereby, in a preferred embodiment, TAA-RNAs or -peptides can be used with the addition of adjuvants, or can also be used alone. As adjuvant, for example, the granulocyte-macrophage-colony-stimulating-factor (GM-CSF) can be used. Further examples for such adjuvants are aluminium hydroxide, emulsions of mineral oils, such as, for example, Freund's adjuvant, saponins or silicon compounds. The use together with adjuvants offers the advantage that the immune response as triggered can be amplified and/or that the vaccine is stabilized.

The invention in an additional aspect thereof furthermore relates to a pharmaceutical composition containing one or more of the TAA-RNAs or -peptides as identified. This composition serves, for example, for parenteral administration, or, for example, for subcutaneous, intradermal or intramuscular, or for oral administration. Thereby, the RNAs or peptides are dissolved or suspended in a pharmaceutically acceptable, preferably aqueous, carrier. In addition, the composition can contain excipients, such as, for example, buffers, binding agents, diluents, etc.

RNAs or peptides can also be administered together with immune-stimulating substances, such as, for example, cytokines. A comprehensive presentation of auxiliary agents that can be used in such a composition is found, for example, in A. Kibbe, Handbook of Pharmaceutical Excipients, $3^{rd}$ Ed., 2000, American Pharmaceutical Association and pharmaceutical press.

Thereby, the agent can be used for the prevention, prophylaxis and/or therapy of tumourous diseases.

Thereby, the peptide or the peptides or the RNA(s), respectively, are present in the pharmaceutical composition in a therapeutically effective amount. Thereby, the peptides or the peptides as encoded by the RNAs contained in the composition can also bind to at least two different types of HLA.

Particularly preferred is a method according to the present invention, wherein the tumour vaccine or tumour therapeutic being a personalized single vaccine or therapeutic is a multi epitope-vaccine or therapeutic. Thus, the tumour vaccine or tumour therapeutic contains TAAs or T-cells that are specifically adjusted to the patient or the patient group that are able to effectively fight the tumour or the tumours in the patient. As is the case with every form of the individualization of oncologic therapy, thereby the chances for a success of the therapy in the individual case are improved.

In a further aspect of the invention, it relates to a method for treating a tumourous disease, comprising a method as mentioned above, and treatment of the tumourous disease based on the antigen-expression pattern as identified. Finally, the present invention relates to a method for treating a tumourous disease, comprising a method as mentioned above, and treatment of the tumourous disease based on the tumour vaccine or tumour therapeutic as produced. Thereby, the tumourous diseases to be treated comprise as above, for example, kidney, breast, pancreatic, stomach, testicular and/or skin cancer. The effective amount as required for an effective treatment and the route of administration can be readily determined by the attending physician on the basis of patient-specific parameters.

The invention shall now be further illustrated in the following based on the accompanying examples, nevertheless, without being limited thereto. All references as cited herein are incorporated by reference in their entireties for the purpose of the present invention. In the Figures:

FIG. 1 shows an overview over the tumour-associated antigens identified in the patient model MZ2. References for sources: MAGE A-1: Traversari C et al., J Exp Med 1992; 176: 1453-7, van der Bruggen P et al., Eur J Immunol 1994a; 24: 2134-40; MAGE A-3 Gaugler B et al., J Exp Med 1994; 179: 921-30; BAGE Boel P et al., Immunity 1995; 2: 167-75; GAGE 1,2,8 Van den Eynde B et al., J Exp Med 1995; 182: 689-98; GAGE 3,4,5,6,7 De Backer O et al., Cancer Res 1999; 59: 3157-65; Tyrosinase Brichard V G et al., Eur J Immunol 1996; 26: 224-230 and MAGE A-6 Vantomme V et al., Cancer Immun [serial online] 2003; 3: 17.

Figure 2:
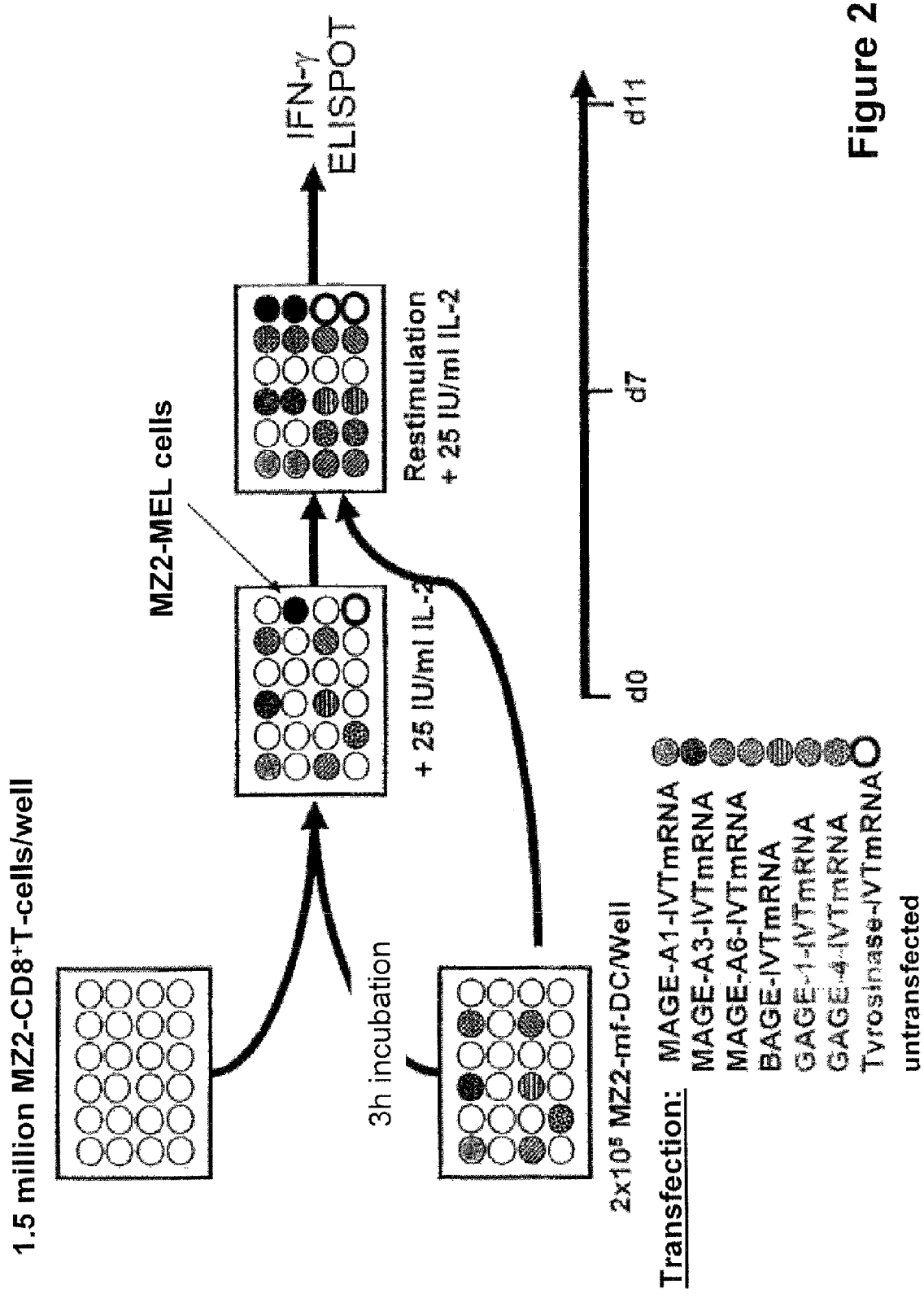

FIG. 2 shows the stimulation assay in a schematic overview.

Figure 3:
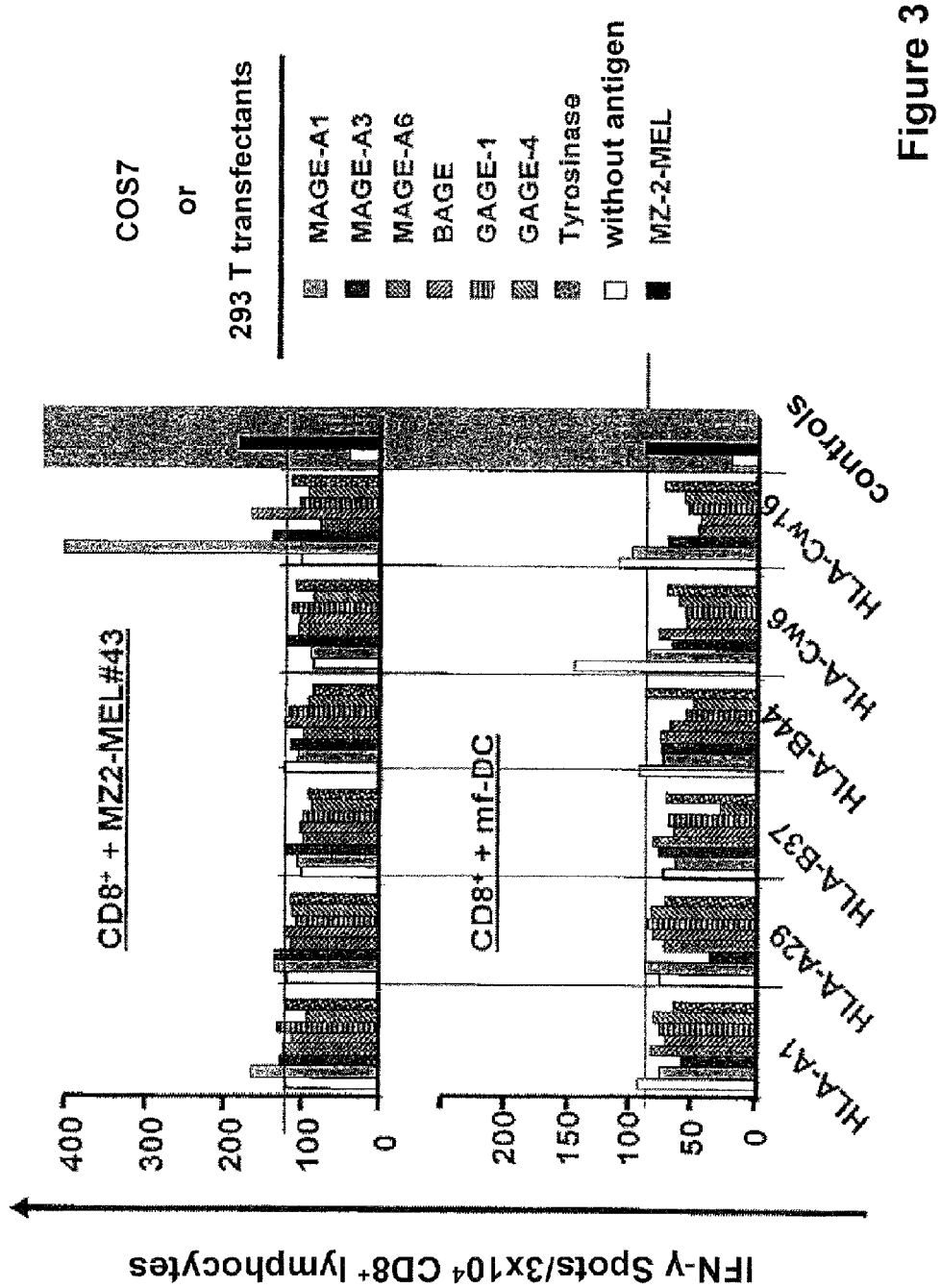
Figure 4:
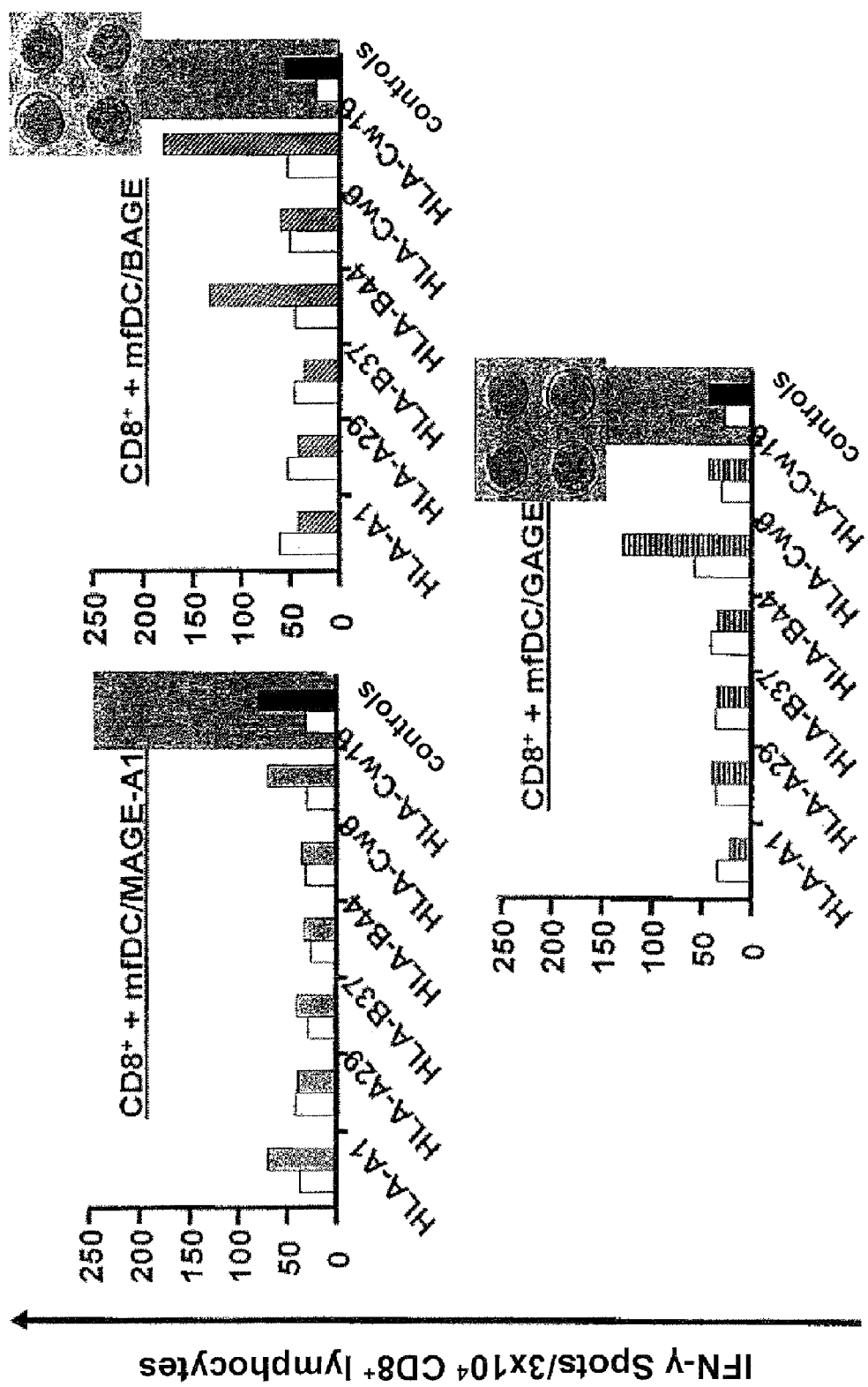
Figure 5:
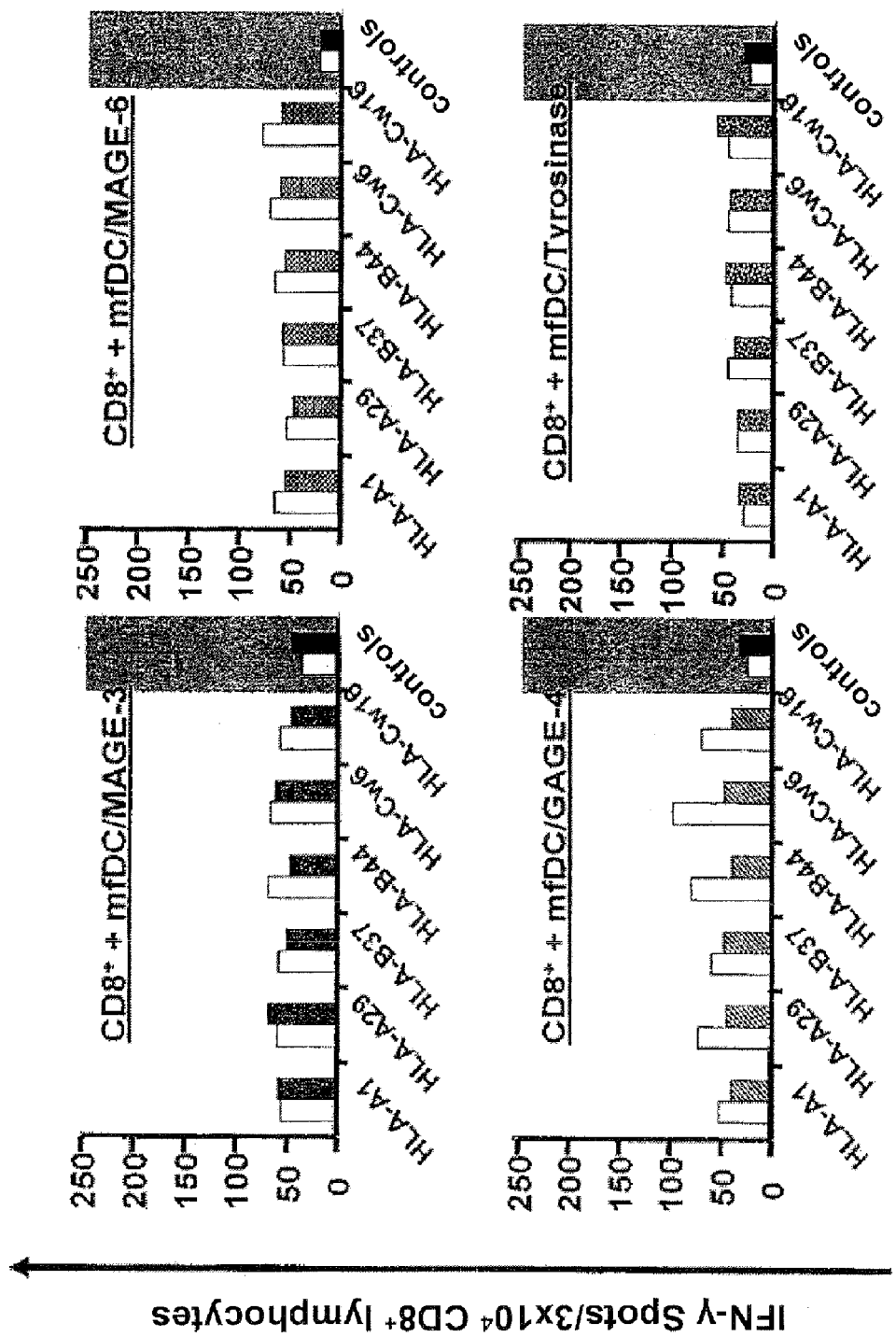

FIGS. 3 to 5 show the reaction analysis of the stimulated CD8+ T-cells of patient MZ2 with tumour cells (FIG. 3), non-transfected DCs (FIG. 3), and with TAA-RNA transfected DCs (FIGS. 4, 5); with tumour cells stimulated T-cells only recognized MAGE-A1/HLA-Cw16-transfectants (FIG. 3 top); with non-transfected DCs stimulated T-cells did not recognize any transfectants (FIG. 3 bottom); T-cells that were stimulated with MAGE-A1-transfected DCs recognized MAGE-A1/HLA-A1- and MAGE-A1/HLA-Cw16-transfectants in the reaction assay (FIG. 4, top left); T-cells that were stimulated with BAGE-transfected DCs, recognized BAGE/HLA-B44- and BAGE/HLA-Cw16-transfectants (FIG. 4, top right); T-cells that were stimulated with GAGE-1-transfected DCs, recognized GAGE-1/HLA-Cw6-transfectants (FIG. 4, bottom); none of the other stimulated T-cells recognized TAA/HLA-transfectants in the reaction assay (FIG. 5).

FIG. 6 shows the summary of the reactivites of the T-cells generated by different methods against all TAAs found in this model.

EXAMPLES

During the last years, the inventors discovered and characterized T-cell-recognized TAAs in several tumour models of melanoma patients. Prerequisites for this were a stable growing tumour cell line for each patient, and lymphocytes isolated from the peripheral blood of the patient. Through stimulations of the T-cells with the autologous tumour cell line in vitro, the inventors were able to generate tumour reactive T-cell populations, and T-cell clones. These were used for the identification of TAAs. Thereby, it could be found that an individual spectrum of TAA/HLA-combinations was recognized by the anti-tumoural T-cells of each of the patients as examined. In every case, new peptide epitopes of differentiation antigens, C/G-antigens as well as mutated antigens were recognized. Only in exceptional cases peptide/HLA-complexes as already known from the literature were confirmed. Obviously, the combination of tumour specific TAA-expression patterns, the individual HLA-type and the ability of the highly variable T-cell repertoires to react to given antigen-combinations leads to individual-specific reaction patterns. Currently, the individuality of these tumour-host-interactions can only be analyzed in individual patient models, since it is possible to generate tumour cell lines for the stimulation of autologous T-cells in vitro only from very few patients. Nevertheless, without the stimulation tumour reactive T-cells from patient blood can not be detected using current methods, since their frequencies in the peripheral blood are too low. Thus, the inventors started to search for a surrogate for tumour cell lines for the stimulation of T-cells from the peripheral blood of tumour patients with TAAs. Immature dendritic cells (iDCs) can be produced from peripheral blood monocytes in vitro and differentiated into mature DCs (mDCs). mDCs are professional antigen-presenting cells that can effectively stimulate T-cells. In two melanoma models, in which 8 (model MZ2) and 13 (D05-GS) T-cell-recognized antigens were known, the inventors transfected mDCs of the patients with the respective antigens and additional control antigens (D05-GS) and stimulated T-cells from the peripheral blood of the patients with the transfected DCs. The inventors chose the messenger-RNA (mRNA) as antigen format. mRNA is suitable for the transient transfection of a multitude of kinds of cells, encodes for the antigens in full length, and thus includes the entirety of possible epitopes. In some earlier studies the suitability of mRNA-transfected DCs for the detection of T-cell responses was examined (Britten et al., J Immunol Methods 287:125, 2004; Britten et al., J Immunol Methods 299:165, 2005). For the scheduled assay in vitro transcribed (IVT) TAA-encoding mRNAs should be transfected into mDCs from peripheral blood of the respective patient. RNA-transfected DCs should serve as stimulator cells for the expansion of TAA-reactive T-cells. The latter should be checked with IFN-γ-ELISPOT-assays. Using the stimulation assay in principle it is possible to identify T-cell reactivities against TAAs in each patient with a kind of tumour for which the expression of a fraction of the antigens is known. Recognized antigens could then be used for the therapeutic immunisation of the patients e.g. in form of a multiepitope-vaccine.

Generation and Transfection of Mature Dendritic Cells from Patients with TAA-encoding mRNAs Both "conventional" mature DC (mDC for mature DC) as well as so-called fastDCs (mfDCs; mature fast DCs) were used for the stimulation of the T-cells with RNA-transfected DCs. mDCs were generated from monocytes of the PBMCs of the patients according to the method of Jonuleit et al. (Eur. J. Immunol. 1997; 27 (12): 3135-42), and mfDCs according to the method of Dauer et al. (J. Immunol. 2003; 170 (8): 4069-76). For the transfection with TAA-RNAs, $2 \times 10^5$ DCs were transfected with 0.8 µg of in vitro-transcribed RNA per reaction using the transmessenger-RNA-transfection reagent (Qiagen, Hilden). Subsequently the cells were incubated for three hours in the incubator.

Stimulation of the T-cells of patients with the Transfected DCs

Directly after the three hour incubation in the incubator the transfected DCs were used for the stimulation of the beforehand isolated CD8+ T-cells of the patients. Thereby $1$-$1.5 \times 10^6$ CD8+ T-cells were stimulated per culture unit (CU) of a 24-well-cell culture plate with $1 \times 10^5$ transfected DCs and $2 \times 10^5$ CD8-negative cells (so-called "feeder-cells", irradiated with 100 gray). Human recombinant interleukin-2 (IL-2; 25 IU/ml) was added as T-cell growth factor. AIM-V-medium (Invitrogen, Karlsruhe) supplemented with 10% human serum (pooled serum of healthy donors) was used as culture medium. In control experiments were the T-cells were stimulated with autologous melanoma cells ($1 \times 10^5$) as well as non-transfected DCs. On day 7 after start of the experiment, the T-cells were restimulated following the same protocol, and an additional 4-5 days later analysed for the recognition of the TAA.

Determination of the Reactivity of the T-cells Against the TAAs used for the Stimulation On day 11 or 12 of the experiment, the CD8+ T-cells were tested for their reactivity against the stimulation-TAAs and the HLA-restriction of the recognition. In order to exclude the unspecific reactivity of e.g. autoreactive T-cells against the DCs, 293T-cells or COS-7-cells were used as antigen-presenting cells for the reaction assay. These were transfected with eukaryotic expression vectors that contained cDNAs encoding for the TAAs. Each TAA-cDNA was co-transfected in individual reactions with the cDNA of each HLA-allele of the patient, and the recognition of the transfectants by the T-cells was examined after 24 hours in an IFN-γ-ELISPOT-assay. Lipofectamine 2000 (Invitrogen, Karlsruhe) was used for the transfection. The assays was performed in accordance with the protocol described in Lennerz et al. (PNAS 2005; 102 (44): 16013-16018). The method as presented was tested on two well characterised patient-models:

I: Model MZ2-MEL

Earlier, eight T-cell recognized TAA/HLA-combinations were identified in the model MZ2 (FIG. 1): MAGE-A1/HLA-A1 (Traversari C. et al., J. Exp. Med. 1992; 176: 1453-7), MAGE-A3/HLA-A1 (Gaugler B. et al., J. Exp. Med. 1994; 179: 921-30), MAGE-A1/HLA-Cw16 (van der Bruggen P. et al., Eur. J. Immunol. 1994a; 24: 2134-4), BAGE-1/HLA-Cw16 (Boel P. et al., Immunity 1995; 2: 167-75), GAGE-1, 2, 8/HLA-Cw6 (Van den Eynde B. et al., J. Exp. Med. 1995;

182: 689-98), tyrosinase/HLA-B44 (Brichard V. G. et al., Eur. J. Immunol. 1996; 26: 224-230), GAGE-3, 4, 5, 6, 7/HLA-A29 (De Backer O. et al., Cancer Res. 1999; 59: 3157-65), and MAGE-A6/HLA-Cw16 (Vantomme V. et al., Cancer Immun. [serial online] 2003; 3: 17). CD8$^+$ T-cells were isolated from PBMCs of the patient and stimulated with DCs that were transfected with each of the eight TAAs in accordance with the above mentioned method (FIG. 2). In the subsequent reaction assay, 4/8 T-cell specificities could be detected (FIGS. 4-6). In addition, a TAA was identified which was not yet discovered: BAGE-1/HLAB44 (FIGS. 4, 6). The T-cells were also stimulated simultaneously with non-transfected DC, as well as with the autologous melanoma cells. Whereas the stimulation with non-transfected DC did not expand TAA-specific T-cell responses, the stimulation with the melanoma cells led to the recognition of the identical TAA-spectrum, as the stimulation with RNA-DCs (Table in FIG. 6).

II: Model D05-GS:

At the time of the stimulation assay, 16 T-cell recognized TAA had been identified in this model. Diverting from the above-mentioned method in the experiment PBMCs were used instead of pre-isolated CD8$^+$ T-cells. Apart from this, the experiment was performed in accordance with the above-mentioned protocol: Aliquots of the PBMCs (1.2×10$^6$/reaction) were stimulated with DCs that were transfected with each of the TAA-RNAs, as well as with non-transfected DCs, and with melanoma cells. After a restimulation on day 7, the T-cells were used in the reaction assay on day 12. The T-cells stimulated with melanoma cells recognized 11 of the 16 known antigens (FIG. 7 bottom, and 10). T-cells stimulated with non-transfected DCs did not recognize any of the antigens (FIG. 7 top), which proves that no unspecific TAA-reactivity is generated. Four of the known reactivities were recognized again by TAA-RNA-stimulated T-cells (FIGS. 8-10). In addition, a specificity was newly discovered (MAGE-C2/HLA-A2), which, as was found in further examinations, could not be detected by the stimulation with the tumour cell clone (clone 6) that was used for the melanoma-stimulation approach, since the tumour clone does not express MAGE-C2. Nevertheless, MAGE-C2 is expressed in the melanoma cell line, from which clone 6 was isolated and which was used for vaccinating patient D05-GS over years. Thereby, the presence of the MAGE-C2-reactive T-cells in the peripheral blood of the patient can be explained. The fact that these T-cells could be detected through the stimulation with MAGE-C2-RNA transfected DCs, underlines the efficiency and specificity of the stimulation assay.

The invention claimed is:

1. A method for identifying the preferential target antigens of anti-tumoural T-cells of at least one tumour patient that is suffering from a specific tumour comprising:
   a) providing T cells from the blood of said at least one tumour patient, wherein the T cells are not stimulated by contact with a tumour cell line in vitro;
   b) providing a panel of transfected dendritic cells (DCs) and/or a panel of transfected B-lymphocytes (BLCs) for said at least one tumour patient, wherein said panel of DCs and/or BLCs are autologous DCs or autologous BLCs transfected with mRNA encoding individual T-cell tumour antigens associated with said specific tumour, wherein multiple T cell tumour antigens are represented within the panel, and wherein said mRNA is provided independent from the extraction of tumour cells from said at least one tumour patient;
   c) contacting the panel of transfected dendritic cells (DCs) and/or transfected B-lymphocytes (BLCs) for said at least one tumour patient with the respective autologous T cells; and
   d) identifying the tumour-associated antigens (TAAs) that are recognized by the T cells on the panel of transfected DCs and/or BLCs for said at least one tumour patient.

2. The method according to claim 1, further comprising the expansion of the T-cells that recognize antigens of the DCs and/or BLCs.

3. The method according to claim 1, further comprising a control assay for the reactivity of the T-cells against the TAA.

4. The method according to claim 1 further comprising determining the HLA alleles by which the recognized TAAs are presented.

5. The method according to claim 1 wherein the T cells are isolated T cells from the blood of said at least one tumour patient.

6. The method according to claim 1 wherein the mRNA encoding the tumour antigens are mRNA encoding antigens of several categories.

7. The method according to claim 6, wherein the antigens are melanocyte-specific proteins or cancer/germline-proteins (C/G-proteins).

8. The method according to claim 6 wherein the categories of tumour antigens are selected from the group consisting of differentiation antigens, cancer/germline antigens (C/G-antigens), mutated antigens and over-expressed antigens.

9. The method according to claim 8 wherein the mutated antigen is a fusion protein.

10. The method according to claim 1 wherein the specific tumour is malignant melanoma.

11. The method according to claim 6, wherein the mRNA encoding the tumour antigens includes structurally normal, "shared" TAAs.

12. The method according to claim 11, wherein said structurally normal ("shared") TAAs are selected from the group consisting of BAGE-1; GAGE-1,2,8; GAGE-3,4,5,6,7; GnTV (intron); HER V-K-MEL; KK-LC-1; KM-HN-1; LAGE-1; MAGE-A1; MAGE-A2; MAGE-A3; MAGE-A4; MAGE-A6; MAGE-A9; MAGE-A10; MAGE-A12; MAGE-C2; mucin; NA-88; NY-ESO-1/LAGE-2; SAGE; Sp17; SSX-2, SSX-4; and TRP2-INT2(intron 2).

13. The method according to claim 1 wherein the specific tumour is a tumour selected from the group consisting of kidney, breast, pancreatic, stomach, testicular, prostate, colon and skin.

* * * * *

UNITED STATES PATENT AND TRADEMARK OFFICE
CERTIFICATE OF CORRECTION

PATENT NO. : 8,349,558 B2
APPLICATION NO. : 12/519315
DATED : January 8, 2013
INVENTOR(S) : Martina Fatho et al.

It is certified that error appears in the above-identified patent and that said Letters Patent is hereby corrected as shown below:

In the Specifications:

Column 4,

Line 42, "B337;" should read --B37;--

Signed and Sealed this
Twenty-first Day of May, 2013

Teresa Stanek Rea
*Acting Director of the United States Patent and Trademark Office*